US010124330B2

(12) United States Patent
Kaasa

(10) Patent No.: US 10,124,330 B2
(45) Date of Patent: Nov. 13, 2018

(54) METHOD AND APPARATUS FOR THE REMOVAL OF POLYVALENT CATIONS FROM MONO ETHYLENE GLYCOL

(75) Inventor: Baard Kaasa, Ranheim (NO)

(73) Assignee: EQUINOR ENERGY AS, Stavanger (NO)

( * ) Notice: Subject to any disclaimer, the term of this patent is extended or adjusted under 35 U.S.C. 154(b) by 486 days.

(21) Appl. No.: 14/125,194

(22) PCT Filed: Jun. 14, 2011

(86) PCT No.: PCT/EP2011/059850
§ 371 (c)(1),
(2), (4) Date: May 8, 2014

(87) PCT Pub. No.: WO2012/171554
PCT Pub. Date: Dec. 20, 2012

(65) Prior Publication Data
US 2014/0235900 A1 Aug. 21, 2014

(51) Int. Cl.
| C07C 29/80 | (2006.01) |
| B01L 3/00 | (2006.01) |
| C07C 29/76 | (2006.01) |
| B01D 3/00 | (2006.01) |

(52) U.S. Cl.
CPC ............... B01L 3/00 (2013.01); C07C 29/76 (2013.01); C07C 29/80 (2013.01)

(58) Field of Classification Search
CPC ...................................................... C07C 27/26
USPC ........................................................ 568/868
See application file for complete search history.

(56) References Cited

U.S. PATENT DOCUMENTS 5,993,608 A * 11/1999 Abry ................ B01D 53/1425
159/48.1
2005/0072663 A1 * 4/2005 Laborie .................. C07C 29/76
203/18

FOREIGN PATENT DOCUMENTS

| CN | 1974509 A | 6/2007 |
| GB | 2473213 | 3/2011 |
| RU | 2128640 C1 | 4/1999 |
| WO | 95/11876 A1 | 5/1995 |
| WO | WO-2005092470 A1 * | 10/2005 | ......... B01D 21/0012 |
| WO | 2007/073204 A1 | 6/2007 |
| WO | WO-2007073204 A1 * | 6/2007 | ............ C07C 29/80 |
| WO | 2009/017971 A1 | 2/2009 |
| WO | 2011/028131 A1 | 3/2011 |

OTHER PUBLICATIONS

International Search Report received for PCT Patent Application No. PCT/EP2011/059850, dated Mar. 6, 2012, 3 pages.
Notification of Grant received for Russian Patent Application No. 2014100906, dated Apr. 29, 2015, 14 pages (6 pages of English Translation and 8 pages of Official copy).
International Preliminary Report on Patentability received for PCT Patent Application No. PCT/EP2011/059850, dated Jan. 3, 2014, 9 pages.
International Written Opinion received for PCT Patent Application No. PCT/EP2011/059850, dated Mar. 6, 2012, 7 pages.
Office Action received for Chinese Patent Application No. 201180071610.5, dated Aug. 22, 2014, 10 pages (English translation only).

* cited by examiner

Primary Examiner — Jeffrey S Lundgren
Assistant Examiner — Michael J Schmitt
(74) Attorney, Agent, or Firm — Wenderoth, Lind & Ponack, L.L.P.

(57) ABSTRACT

The invention relates to a method and an apparatus for the removal of polyvalent cations, in particular divalent cations, from mono ethylene glycol. Mono Ethylene Glycol (MEG) is used to prevent hydrate formation in pipelines transporting gas, condensate and water. It may also contribute to pipeline corrosion control. The invention describes a method for the removal of polyvalent cations from mono ethylene glycol, comprising providing a feed of aqueous mono ethylene glycol comprising dissolved gas and salts of divalent cations (rich MEG), heating the aqueous mono ethylene glycol to a heated mixture, causing precipitation of at least part of the salts and release of at least part of the dissolved gas, in particular carbon dioxide, separation of released gas from the mono ethylene glycol, separation of at least part of the precipitated salts from the mono ethylene glycol, distillation of at least part of the water from the heated mixture, to yield hot dewatered mono ethylene glycol (lean MEG), wherein a first part of the hot dewatered mono ethylene glycol is lead back to the aqueous mono ethylene glycol feed to provide at least part of the heat for heating the aqueous mono ethylene glycol.

8 Claims, 1 Drawing Sheet

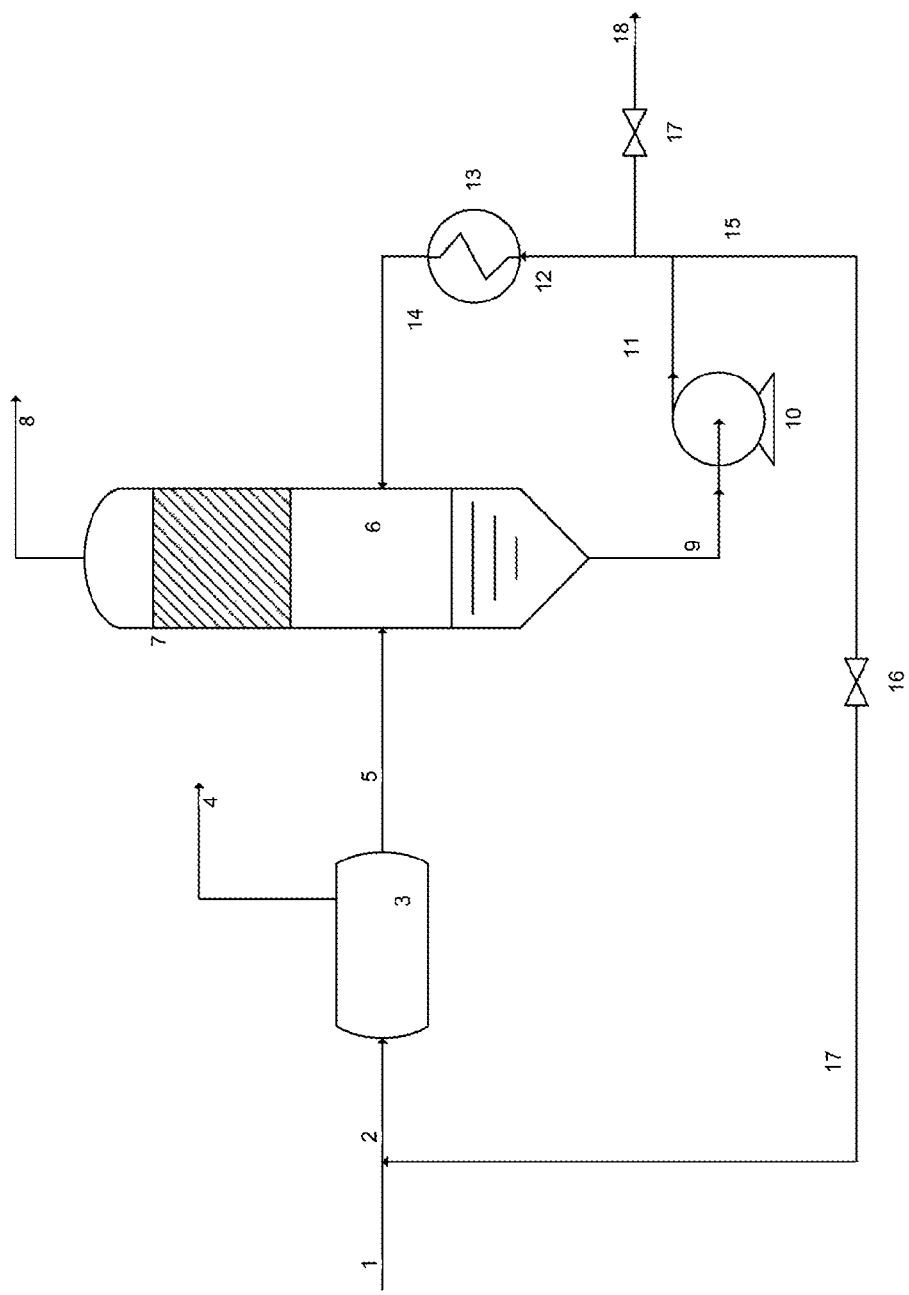

METHOD AND APPARATUS FOR THE REMOVAL OF POLYVALENT CATIONS FROM MONO ETHYLENE GLYCOL

CROSS REFERENCE TO RELATED APPLICATIONS

This application is a U.S. National Phase Patent Application of PCT/EP2011/059850, filed on Jun. 14, 2011, which is hereby incorporated by reference in the present disclosure in its entirety.

FIELD OF THE INVENTION

The invention relates to a method and an apparatus for the removal of polyvalent cations, in particular divalent cations, from mono ethylene glycol.

BACKGROUND OF THE INVENTION

Mono Ethylene Glycol (MEG) is used to prevent hydrate formation in pipelines transporting gas, condensate and water. It may also contribute to pipeline corrosion control. Typically, a 90 wt % MEG solution is injected to the gas stream at the beginning of the pipeline. A water phase may or may not be present at the pipeline inlet. As the stream cools down though the pipeline, water will condense from the gas. Water and MEG will mix completely and the mixture of aqueous methyl ethylene glycol is called rich MEG, because it is rich in water. The MEG concentration in the rich MEG can be 30-80 wt %, typically 50-65 wt %.

The rich MEG is separated from the gas and the condensate in one or several separation stages. Normally the rich MEG is heated to 30-80° C. to improve separation and avoid formation of emulsions/foam. Filters, centrifuges, decanters, coaleshers etc. may be included to improve the separation process and for removal or particles. The rich MEG is then normally sent to a storage/buffer tank, before it is sent to a regeneration unit to remove impurities. The processing of rich MEG is called pre treatment.

MEG is regenerated in a regeneration unit which typically consist of a reboiler/heater and a distillation column. The rich MEG is heated in the reboiler and most of the water is evaporated to produce the desired MEG concentration in the reboiler, normally around 90 wt %. The feeding point may be either directly into the reboiler or in the distillation column. The vapour is distilled to remove MEG and produce water with as low MEG concentration as possible, typically below 1000 ppm.

The rich MEG may contain many contaminants, such as ions, particles and various production chemicals. Especially troublesome are divalent cations such as iron, calcium, barium, strontium and magnesium because they can precipitate as various carbonates and hydroxide salts in the regeneration system. Carbonate salts from divalent cations tend to precipitate on hot surfaces because their solubility decreases with increasing temperature. To avoid scale problems in the reboiler, these ions should be removed from the rich MEG before entering the reboiler or other distillation equipment.

A solution for chemically removing certain salts from MEG is described in WO 2009/017971, which describes a reclamation unit that removes the salt as a pre-treatment before distillation, by adding chemicals such as NaOH, NaHCO3, Na2CO3 to increase pH and carbonate concentration. This will lead to high super saturation of the carbonate salts of the divalent cations and they will thus precipitate and can be filtered off.

If chemicals are added, they will accumulate in the MEG unless they are taken out later. Adding NaOH, NaHCO3, Na2CO3 or similar to increase pH means that sodium concentration increases and also the alkalinity. (It is also possible to use the similar potassium salts). A reclaimer stage may have to be included to control the salt concentration level in the loop. Having to use the reclaimer makes the process more complicated in addition to increased chemical costs and relatively high energy consumption.

Another solution is to precipitate polyvalent cations by preheating the MEG. This can be done by a preheater unit positioned before the distillation unit. Heating the rich MEG will lead to salt precipitation, which may subsequently be removed by some solids removal process such as filtering, centrifuge or settling. Heating alone may, however, be insufficient to get quantitative precipitation of the divalent cations and the reaction rate can be slow, requiring a large flash drum or similar tank to increase the retention time.

OBJECT AND SUMMARY OF THE INVENTION

It is an object of the invention to provide a method for removing polyvalent cations from aqueous MEG that is relatively simple. It is another object of the invention to provide a method to remove polyvalent cations from aqueous MEG that has a relatively low energy consumption and without additions of any chemicals.

The invention provides a method for the removal of polyvalent cations, in particular divalent cations, from mono ethylene glycol, comprising the steps of:
a) providing a feed of aqueous mono ethylene glycol (rich MEG) comprising dissolved gas and salts of divalent cations,
b) heating the aqueous mono ethylene glycol to a heated mixture, causing precipitation of at least part of the salts and release of at least part of the dissolved gas, in particular carbon dioxide,
c) separation of released gas from the mono ethylene glycol,
d) separation of at least part of the precipitated salts from the mono ethylene glycol,
e) distillation of at least part of the water from the heated mixture, to yield hot dewatered mono ethylene glycol (lean MEG),
wherein a first part of the hot dewatered mono ethylene glycol is lead back to the aqueous mono ethylene glycol supplied in step a) to provide at least part of the heat for heating the aqueous mono ethylene glycol in step b).

The feed of aqueous MEG, also called rich MEG, can have various sources, but is typically derived from a gas transport pipeline. The rich MEG stream typically comprises a MEG concentration of 30-80 wt %, preferably 50-65 wt %. The temperature is typically from 5-100° C., preferably 30-60° C. The pressure may vary from atmospherical pressure to 50 bar, typically in the range of 1-5 bar. The multivalent cations present in the rich MEG stream may comprise various elements, for instance Ca, Mg, Ba, Sr. Iron cations, which may exist in various oxidation states, are particularly troublesome if they would precipitate on the surface of equipment, and may be present in concentrations of for instance 0-150 ppm, typically 5-30 ppm. The solution will typically also comprise monovalent cations, in particular sodium. The dissolved gases would typically include carbon dioxide as a main component. Sodium and carbon dioxide are typically present in the form of the corresponding salts, in particular NaHCO$_3$.

Heating of the rich MEG induces precipitation of the polyvalent cations. Once precipitated as salts, the obtained particles may be removed by for instance filtration at a later stage in the process. The solid particles are less prone to settle on equipment than the dissolved cations. Thus, when equipment such as a reboiler is to be protected, most of the precipitation should take place before the mixture is introduced into the reboiler.

The removal of gas, in particular carbon dioxide, assists in precipitating salts. Carbon dioxide is an acid when dissolved with water, and removal will raise the pH of the mixture. The gas removal, for instance in a flash separator under reduced pressure, will further enhance the reaction rate of precipitation. The combination of gas separation and heating will lead to a useful precipitation rate.

The separation of at least part of the precipitated salts from the mono ethylene glycol may be done at one or more places in the process stream, although it is preferred if this is done at the output stream of MEG before further transport or storage.

During distillation of the rich MEG, the temperature is further raised and water is mostly removed, in order to obtain dewatered MEG, also called Lean MEG. In lean MEG, the concentration of MEG is raised due to the removal of water, having concentrations of 70-99 wt %, preferably 85-95 wt %. The temperature of the liquid in the distillation phase, typically using a reboiler, is usually in the range of 100-160° C., preferably 120-150° C. The pressure is typically in the range of 1-2 bar. As the distillation will remove water as well as remaining carbon dioxide, the pH will be higher than the rich MEG, typically in the range of pH 9-14, preferably pH 10-12. At the distillation stage, the mixture would contain precipitated salts. As most of the precipitation was already induced before entering the distillation, by preheating and preliminary removal of carbon dioxide, the precipitation on the warm surfaces of the distillation equipment, in particular the reboiler, would be significantly reduced compared to direct introduction of rich MEG. Part of the dewatered (lean) MEG can be collected for storage, after filtering or otherwise separating the precipitated salts containing polyvalent cations. In the method according to the invention, at least part of the relatively hot lean MEG will be reintroduced into the feed of aqueous (rich) MEG. This provides a means of heating the aqueous MEG to induce new precipitation. This also allows to perform the preheating without a dedicated preheater, or with a preheater that has a lower capacity, making the process and the used equipment simpler, easier and more compact. By monitoring the temperatures of the lean MEG and rich MEG, the amount of hot lean MEG lead back to the feed line to achieve the desired preheating temperature can be determined and controlled.

It is preferred if in step b), the aqueous mono ethylene glycol is heated to at least 60° C., preferably from 60° C. 120° C., most preferably approximately 80-100° C. At such temperatures, precipitation and release of carbon dioxide is induced at an efficient rate.

Preferably, the hot dewatered monoethylene glycol lead back to the feed has a temperature above 100° C., preferably above 120° C., most preferably approximately 145° C. Depending on the starting temperature of the rich MEG feed typically in the range of 30-60° C., this allows to mix in a relatively low amount of lean MEG into the rich MEG feed. It is preferred if the volume ratio of lean MEG to rich MEG is from 1:5 to 5:1. Preferably, the mixture of rich MEG and lean MEG would comprise from 30-80 volume % lean MEG, most preferably around 50-70 volume % lean MEG.

The temperature of the lean MEG is measured at the position where the split off part leaves the distillation unit. Preferably, the amount of hot dewatered monoethylene glycol lead back to the feed is controlled to obtain a warm aqueous monethylene glycol mixture in the temperature range of 60° C. 120° C. in step b), for instance by using control valves or mixing equipment.

In a preferred embodiment the hot dewatered monoethylene glycol (lean MEG) lead back to the feed comprises particles of salts of divalent cations. The particles already present in the returned lean MEG act as nucleation sites and further enhance the rate of precipitation after heating. Also, this prevents precipitation on equipment as the precipitation rate on a preformed particle is usually faster than precipitation on the surface of equipment.

If the separation of at least part of the precipitated salts from the mono ethylene glycol d) is performed on a second part the hot dewatered mono ethylene glycol that is not lead back to the feed. Having particles in the returned hot lean MEG stream may be achieved by separating particles the MEG after the destillation, or only partial separation, or by only separating particles from the MEG that is taken out of the process for further transport or storage. This uses the separation units such as filters more efficiently, and simplifies the control of the process significantly.

It is preferred if in distillation step e) the dewatered monoethylene glycol is circulated in a distillation loop comprising at least one heater, wherein a first part of the dewatered monoethylene glycol lead back to the feed is taken from the circulating monoethylene glycol. Many distillation units comprise a circulation loop, and taking the dewatered MEG from the circulation loop makes it easier to provide a stable and more homogenous stream of hot lean MEG back to the feed, making the process more controllable. Most preferably, the dewatered monoethylene glycol is taken from the distillation loop after distillation and before the heater.

Most preferably, the distillation loop comprises a circulation pump, wherein the dewatered monoethylene glycol is taken from the loop after the recirculation pump and before the heater. This allows the pressure from the recirculation pump to be used for returning the lean MEG to the feed without need for a separate pump.

It is preferred if the salts of polyvalent cations in the monoethylene glycol comprises salts derived from at least one of the elements selected from the group consisting of iron, calcium, barium, strontium and magnesium, or mixtures thereof. The precipitates salts are typically a mixture of carbonate salts, hydroxides and oxides. In a preferred embodiment, the salts comprise iron salts. Iron salts are most preferably removed from MEG, as these are among the most difficult species to remove from the surface of equipment once precipitated there.

The invention further provides an apparatus for the removal of polyvalent cations from mono ethylene glycol comprising a feed line for a feed of aqueous mono ethylene glycol, connected to a flash separator, for separating released gas and precipitating salts from aqueous mono ethylene glycol, wherein the flash separator is coupled to—a reboiler provided with a distillation unit for removing water from the mixture supplied therein by heating, having an outlet to supply at least partially cleaned mono ethylene glycol, —wherein the outlet is provided with a loop back to supply at least part of the hot cleaned mono ethylene glycol to the supply line for aqueous mono ethylene glycol, adapted for heating the feed in the feed line by mixing, wherein the loop back is connected to the feed line upstream from the flash separator. This equipment is adapted for performing the method as described herein. As described above, the reboiler for distillation may comprise a recirculation loop with a recirculation pump, wherein the recirculation pump is positioned to also provide pressure for the loop back.

In a preferred embodiment, the feed line is provided with a preheater, wherein the loop back is introduced into the feed after the preheater. The preheater makes it easier to control the temperature for precipitation when combined with the heat provided by the recirculated lean MEG. Having a preheater also makes it easier and faster to start up the process, for instance after maintenance.

BRIEF DESCRIPTION OF THE DRAWINGS

FIG. 1 describes an example of a process and apparatus for removing polyvalent cations from monoethylene glycol.

DESCRIPTION OF PREFERRED EMBODIMENTS

An example of the process and system is described in detail in FIG. 1. The rich MEG (1) containing the ions is mixed with a hot lean MEG stream (17). The mixed stream (2) should have a temperature in the range 60-120° C., typically 80° C. before it enters a flash separator (3) where the precipitation will occur. Due to the heating, at least part of the dissolved gas is released and is vented off (4).

The hot mixture (5) is then fed to the reboiler unit (6). The feed point is preferably located directly into the reboiler, but may also be located in the recirculation stream (9, 11, 12, 14), preferably downstream from the heater. The liquid phase in the reboiler (6) is circulated (9) by a circulation pump (10) via (11, 12) to a heater (13) where the circulating liquid is heated before it is lead back to the reboiler (6). Water, MEG and other volatile components will evaporate and go to a distillation tower (7) where MEG is condensed and drained back to the reboiler (6). The water vapour leaving the top (8) of the distillation column is condensed in a standard reflux system. Part of the condensed water is used for reflux in the column (not shown in the FIGURE).

In the regeneration process, the rich MEG is boiled to evaporate water to produce typically 90 wt % MEG, called lean MEG. Since water is evaporated, there is less solvent to dissolve ions and they are concentrated. The alkalinity of the mixture will therefore increase, leading to increase in pH. Another important factor is that during boiling, remaining $CO_2$ and other gasses are stripped off the mixture. Rich MEG typically has a pH of 5-8, meaning that most of the dissolved $CO_2$ is in the form of bicarbonate ($HCO_3^-$). When $CO_2$ is stripped off, the bicarbonate is converted to carbonate ($CO_3^{2-}$) and this further increases the pH:

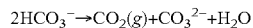
$$2HCO_3^- \rightarrow CO_2(g) + CO_3^{2-} + H_2O$$

The lean MEG solution thus has higher MEG concentration, higher alkalinity, more carbonate and higher pH. All these are factors that will promote precipitation of carbonate salt of the divalent/polyvalent cations.

In the present invention, some of the hot lean MEG (typically 145° C.) is recirculated and mixed with the cold rich MEG to obtain a temperature in the range 60-120° C., typically about 80° C. It is also possible to use a combination of inline heating and recirculation to both obtain the optimum recirculation rate and the optimum temperature. Due to the increased temperature, MEG concentration, alkalinity, carbonate concentration and pH, a substantial percentage of the divalent cations will precipitate fast.

Part of the liquid in the reboiler or the circulation loop is taken out as stream (15) and recirculated by a control valve (16) and injected to the rich MEG stream as (17). The correct composition of the lean MEG is obtained by keeping the temperature/pressure in the reboiler. Lean MEG product is taken out at the outlet (18). The lean MEG stream (18) will contain precipitated particles of polyvalent cation salts, and these are removed by a solids separation process before the lean MEG is sent to storage/injected, preferably by a centrifuge or filtration unit placed in the outgoing MEG stream 18 (not included in the FIGURE).

Alternatively, the filtration unit may also be located at stream (5) or in the circulation loop (9)-(14) to remove at least part of the solid particles. It is also possible to have multiple filtration units at various locations in the process. However, it was found that it is beneficial to have particles present to act as nucleation sites in the heaters, flash drum and reboiler. The recirculating lean MEG (15) may be taken from several locations such as directly from the reboiler (6) or from the outlet pipe (9). This will, however, require an extra recirculation pump. By taking it from stream (11), the discharge pressure of the recirculation pump is used to inject the lean MEG into the rich MEG.

The amount of lean MEG to be returned to the aqueous MEG is determined by the temperature of the lean MEG and the temperature of the incoming aqueous MEG feed 1. By monitoring the temperatures the amount of recirculated hot lean MEG can be adjusted using the control valve 16, in order to raise the temperature of the aqueous MEG feed to the desired temperature range of 60-120° C. Optionally, a preheater may be placed before the flash separator 3 in order to assist in controlling the temperature, and for starting up the process.

The invention claimed is:

1. A method for the removal of polyvalent cations from mono ethylene glycol, comprising the steps of:
    a) providing a feed of aqueous mono ethylene glycol comprising dissolved carbon dioxide and salts of divalent cations,
    b) heating the aqueous mono ethylene glycol to 60° C.-120° C. to produce a heated mixture, causing precipitation of at least part of the salts and release of at least part of the dissolved carbon dioxide,
    c) separating the at least part of the released carbon dioxide from the mono ethylene glycol in a flash separator,
    d) separating the at least part of the precipitated salts from the mono ethylene glycol, and
    e) distilling at least part of the water from the aqueous heated mixture in a reboiler, to yield hot dewatered mono ethylene glycol, wherein the temperature of the liquid in the distillation phase is 120° C.-150° C.,
        wherein a first part of the hot dewatered mono ethylene glycol comprising particles of salts of divalent cations is led back to the feed of aqueous mono ethylene glycol provided in step a) to provide at least part of the heat for heating the aqueous mono ethylene glycol in step b), and
        wherein the separating of the at least part of the precipitated salts from the mono ethylene glycol in step d) is performed on a second part of the hot dewatered mono ethylene glycol that is not led back to the feed.

2. The method according to claim 1, wherein the first part of the hot dewatered mono ethylene glycol led back to the feed has a temperature above 100° C.

3. The method according to claim 1, wherein the amount of the first part of the hot dewatered mono ethylene glycol led back to the feed is controlled to obtain a heated mixture of aqueous mono ethylene glycol having a temperature in the range of 60° C.-120° C. in step b).

4. The method according to claim 1, wherein in the distilling step e) the hot dewatered mono ethylene glycol is circulated in a distillation loop comprising at least one heater, wherein the first part of the hot dewatered mono ethylene glycol led back to the feed is taken from the distillation loop.

5. The method according to claim 4, wherein the first part of the hot dewatered mono ethylene glycol is taken from the distillation loop after distillation and before the heater.

6. The method according to claim 4, wherein the distillation loop further comprises a circulation pump, and wherein the first part of the hot dewatered mono ethylene glycol is taken from the distillation loop after the circulation pump and before the heater.

7. The method according to claim 1, wherein the salts of polyvalent cations in the mono ethylene glycol are salts of at least one element selected from the group consisting of iron, calcium, barium, strontium and magnesium.

8. The method according to claim 7, wherein the salts are predominantly iron salts.

* * * * *